United States Patent

Igaue et al.

[11] Patent Number: 5,807,370
[45] Date of Patent: Sep. 15, 1998

[54] LIQUID ABSORBING SHEET MATERIAL

[75] Inventors: Takamitsu Igaue; Tsutomu Kido, both of Kawanoe; Ryohei Sakakibara, Kobe; Masaharu Sugie, Osaka, all of Japan

[73] Assignee: Uni-Charm Corporation, Ehime, Japan

[21] Appl. No.: 787,450

[22] Filed: Jan. 22, 1997

Related U.S. Application Data

[63] Continuation of Ser. No. 329,962, Oct. 27, 1994, abandoned.

[30] Foreign Application Priority Data

Dec. 29, 1993 [JP] Japan ............................ 5-353119
Dec. 29, 1993 [JP] Japan ............................ 5-353120

[51] Int. Cl.$^6$ ................................ A61F 13/15
[52] U.S. Cl. .................. 604/383; 604/378; 604/384; 442/402; 442/403
[58] Field of Search .................... 604/378, 369, 604/383, 384; 442/402–408

[56] References Cited

U.S. PATENT DOCUMENTS

| | | | |
|---|---|---|---|
| 3,122,140 | 2/1964 | Crowe, Jr. ............................ | 604/369 |
| 3,122,142 | 2/1964 | Crowe, Jr. ............................ | 604/369 |
| 3,156,242 | 11/1964 | Crowe, Jr. ............................ | 604/369 |
| 3,937,861 | 2/1976 | Zuckerman et al. .................. | 442/402 |
| 3,950,587 | 4/1976 | Colijn et al. ........................ | 442/402 |
| 4,377,615 | 3/1983 | Suzuki et al. ........................ | 604/365 |
| 4,723,954 | 2/1988 | Pieniak ................................ | 604/384 |
| 4,826,498 | 5/1989 | Koczab ................................ | 604/383 |
| 5,401,267 | 3/1995 | Couture-dorschner et al. ...... | 604/358 |
| 5,423,787 | 6/1995 | Kjellberg ............................. | 604/378 |

FOREIGN PATENT DOCUMENTS

| | | |
|---|---|---|
| 1144110 | 3/1969 | United Kingdom . |
| 2190111 | 11/1987 | United Kingdom . |
| 2214201 | 8/1989 | United Kingdom . |

*Primary Examiner*—John G. Weiss
*Assistant Examiner*—Dennis Ruhl
*Attorney, Agent, or Firm*—Armstrong, Westerman, Hattori, McLeland & Naughton

[57] ABSTRACT

A liquid-absorbing sheet material is prepared by spraying fibers of a molten liquid conveyable material onto a surface of a one- or two-layer fabric base material while applying a vacuum to the opposite surface. The fibers of the liquid conveyable material permeate the one- or two-layer base material.

8 Claims, 5 Drawing Sheets

LIQUID ABSORBING SHEET MATERIAL

This application is a continuation of application Ser. No. 08/329,962 filed Oct. 27, 1994, now abandoned.

FIELD OF THE INVENTION

This invention relates to a liquid absorbing sheet material useful as a covering material for a surface layer of sanitary articles such as disposable diapers, sanitary napkins, and surgical absorbing sheet. It also relates to a method for producing the sheet material and sanitary articles produced using the sheet material.

BACKGROUND OF THE INVENTION

Generally, a sanitary article such as a disposable diaper and a sanitary napkin comprises a liquid absorbing material, a polyethylene sheet arranged on a reverse side of the liquid absorbing material for preventing liquid from leaking, and a covering material made of a non-woven fabric, which covers the whole of the liquid absorbing material, and the polyethylene sheet. The absorbing property of such sanitary articles greatly depends on the liquid permeability of the covering material. It is most desirable that excreted body fluid immediately passes through the covering material surface made of non-woven fabric without staying thereon and passes to the liquid absorbing material inside such that the covering material surface is maintained dry so as not to feel wet to a user.

Heretofore, a cellulose material has been employed as the covering material, but such a material does not meet the above requirements. Replacing the cellulose material with a polyester or polypropylene material has come into use. However, even when either a polyester or a polypropylene material is employed, poor permeability results, and excreted body fluid forms water drops on the surface. To solve such a problem, such a covering material is made liquid permeable by conducting a surface active agent treatment by soaking, spraying, baking the covering material with a surface on the surface based active agent. Such a base non-woven fabric for the covering material can be obtained, for example, by preparing a web from non-woven fabric material and adhering the web with an adhesive. Subsequently, the thus obtained non-woven fabric is formed into a sheet and wound up in rolls. The covering material can be manufactured by employing a non-woven fabric wound up in a roll, and withdrawing the non-woven fabric from the wound-up roll, treating the fabric with a surface active agent and finally winding the non-woven fabric into another roll.

First or the second excretions of body fluid at the initial stages can permeate smoothly through the above surface active agent treated non-woven fabric. However, such a non-woven fabric has a drawback in that permeability deteriorates as more body fluid is excreted since the surface active agent starts to escape, resulting in deterioration of the permeability. Also, when a non-woven fabric is treated with a surface active agent to give permeability, its surface becomes wet so it feels uncomfortable to the user.

In addition, as the prepared non-woven fabric is usually shaped as a sheet, which is usually wound up in a roll, lowering of the transportation speed in changing rolls on a manufacturing line is required. In order to improve productivity, the length of the non-woven fabric sheet for a roll must be as long as possible. However, the thickness of the non-woven fabric in a roll shape is limited. An increase in the length of a non-woven fabric for a roll has been achieved by lowering the METSUKE volume as much as possible so as to decrease the thickness. The lower limit of the METSUKE volume is about 20 $g/m^2$. With a lower METSUKE volume, the resultant non-woven fabric becomes uneven, and, adhesive in the fabric often bleeds.

OBJECT OF THE INVENTION

It is an object of the invention to provide a liquid absorbing sheet material, a method of manufacturing the liquid absorbing sheet material, a method of manufacturing a sheet material and sanitary articles containing the liquid sheet absorbing material.

DISCLOSURE OF THE INVENTION

In order to accomplish the above object, the first aspect of the present invention is a liquid absorbing sheet material wherein a fibrous body made of a liquid conveyable material is scattered extending from the reverse side to the surface of a fabric tissue of a fabric base material. The second aspect is a liquid absorbing sheet material containing a first fabric base material and a second fabric base material having heat fusible polymer laminated on one side of the first fabric base material. A fibrous body made of liquid conveyable material is scattered extending from the reverse side to the surface of the fabric tissue comprising the two-layer first fabric base material and the second fabric base material. The third aspect is a method of preparing a liquid absorbing sheet material comprising moving a sheet of first fabric base material, forming a second fabric base material on the first fabric base material by spraying a heat fusible polymer on reverse side of the first fabric base material and spraying a fibrous body comprising a liquid conveyable material on the reverse side of the second fabric base material so as to have the liquid conveyable material penetrate both tissues of the first fabric base material and the second fabric base material. The fourth aspect is a method of preparing sheet material comprising moving a sheet of a first fabric base material and forming a second fabric base material on the fabric base material by spraying heat fusible polymer on the first fabric base material. Lastly, the fifth aspect is a sanitary article wherein the liquid absorbing sheet material of the invention is arranged on the reverse side of the liquid absorbing sheet material.

The present invention is liquid absorbing sheet material, wherein a fibrous material contains a liquid conveyable material in a fabric base material which extends from the reverse side to the surface. Alternately, the above single layer fabric base material can be substituted by a two-layer fabric base material of a first and second fabric base material comprising a heat fusible polymer laminated on the one side of the first fabric base material. A fibrous body made of a liquid conveyable material is scattered through the two-layer fabric base material. This liquid absorbing sheet material causes liquid to permeate from the surface to the reverse side of the base material maintaining the surface dry, while absorbing moisture several times without deterioration of the permeability of moisture. The second fabric base material in the two-layer fabric base material has a heat fusible polymer laminated on one side of the first fabric base material, and can be formed by forming a second fabric base material layer on the reverse side of the first fabric base material by spraying a heat fusible polymer on reverse side of a moving first fabric base material and then spraying a fibrous body made of liquid conveyable material on the reverse side of the second fabric base material causing the liquid conveyable material to penetrate tissues of both the first base fabric material and the second fabric base material.

A two-layer sheet material can be obtained by spraying a heat fusible polymer on the reverse side of the first fabric base material to form the second fabric base material layer on the reverse side of the moving first fabric base material. The resultant liquid absorbing sheet material or sheet material is thick and uniform, and a thin sheet of the first fabric base material can be employed. Using a thin sheet material, changing rolls requires less time.

The present invention is now described in further detail.

The liquid absorbing sheet material of the present invention has two embodiments. The first embodiment of the liquid absorbing sheet material is single layer structure, and can be obtained by employing a fabric base material and a liquid conveyable material which makes the fabric base material permeable. The second embodiment of the liquid absorbing sheet material comprises a two layer structure of a first fabric base material and a second fabric base material, and can be obtained by employing a first fabric base material, a heat fusible polymer forming the second fabric base material and a liquid conveyable material which makes the fabric base material permeable. As used herein, a liquid conveyable material means a material that is not water-soluble and is hydrophilic.

The first embodiment of the liquid absorbing sheet material will now be described.

As the fabric base material employed for the first embodiment, there are no limitations and any known material can be employed, such as a union fabric, a non-woven fabric or the like, a non-woven fabric is preferable. As the non-woven fabric, a non-woven fabric whose METSUKE volume is low is preferable. The METSUKE volume of the non-woven fabric should not be more than 20 g/m$^2$, so as not to cause problems during manufacturing. As the non-woven fabric, a 20 to 60 g/m$^2$ METSUKE volume is preferable, a 25 to 50 g/m$^2$ is more preferable and a 30 to 40 g/m$^2$ is most preferable. If the METSUKE volume falls within the above range, a fibrous body made of liquid conveyable material, as described later, permeates into the fabric base material so as to adequately disperse therein. The thickness of the fabric base material is preferably within a range of 0.1 to 3 mm.

As liquid conveyable material to make the fabric base material into liquid conveyable one, a heat fusible polymer is preferred. Such heat fusible polymers are polyolefins such as polypropylene (PP), polyethylene (PE), copolymers of PP and PE, styrene-isoprene block copolymers (SIS), styrene-butadiene block copolymers (SBS), hydrogenated SISs (SEPS), hydrogenated SBSs (SEBS) and the like. These can be employed alone or in combinations of two or more. The SEPS and SEBS are preferable due to their thermal stability. If a water soluble polymer were employed as the liquid conveyable material, the polymer would dissolve by contact with moisture, causing blocking of the texture of the fabric base material.

As the liquid conveyable material, a heat fusible polymer or polymers can be employed alone, but it is preferable that a surface active agent is present. A more effective liquid conveyable property results if the fibrous body is mixed with a surface active agent when forming the fibrous body from a heat fusible polymer. Suitable surface active agents are a nonionic surface active agent having one or two esters, which is fatty acid ester of polyethylene glycol or glycerine, a nonionic surface active agent, which is a block copolymer of polyethylene glycol and polypropylene glycol. The surface active agent is employed at the ratio of 0.1 to 20% by weight (abbreviated as % hereinafter), preferably at the ratio of 0.5 to 10%, to the whole heat fusible polymer to be kneaded with the polymer at a high temperature.

A method for forming a liquid absorbing sheet material of the first embodiment will now be described. The liquid absorbing sheet material of the first embodiment can be manufactured, for example, in the following method. The liquid absorbing sheet material can be prepared by melting the liquid conveyable material substantially composed of heat fusible polymer by heating and spraying it on the reverse side of the fabric base material. As shown in FIG. 1, a vacuum apparatus 2 is positioned under a non-woven fabric sheet 1, moving in direction of an arrow A, while a heat fusible polymer 3 (liquid conveyable material) is sprayed over the reverse of the non-woven fabric sheet 1. Air is used to spray the heat fusible polymer 3 circumferentially immediately after being exhausted from an exit 6 inside an applicator 4 for spraying. The polymer 3 changes into a fibrous state to be sprayed on the reverse side of the non-woven fabric sheet 1 and permeates into the non-woven fabric sheet 1. A liquid absorbing sheet material is thus manufactured.

Thus manufactured liquid absorbing sheet material, as shown in FIG. 2, has a structure wherein a fibrous body formed from the heat fusible polymer 3 (liquid conveyable material) scatters from the reverse to the surface side throughout the fiber 5 of the non-woven fabric 1. The thickness of the resultant fibrous body containing the heat fusible polymer 3 is between about 0.3 to 3 denier.

As method for the spraying, a polymer spray applicator for spraying heat fusible polymer can be used. Samples of such applicators use hot melt spray, spiral spray and the like. If a melt-blown applicator 7, as shown in FIG. 3, is employed, a uniform spraying of the heat fusible polymer 3 on the reverse side of the fabric base material can be realized regardless of a line speed, which is preferable. In FIG. 3, 9 is an exit.

The liquid absorbing sheet material of the second embodiment will now be described.

The absorbing sheet material of the second embodiment, as mentioned before, has a two-layer structure of a first fabric base material and a second fabric base material and can be obtained by employing the fabric base material and the heat fusible polymer forming the second fabric base material, and the liquid conveyable material which renders those two materials permeable.

As the first fabric base material, the same fabric base material as that of the liquid absorbing sheet material in the above first embodiment can be employed.

In addition, as the heat fusible polymer forming the second fabric base material layer, various heat fusible polymers such as a polyolefin of PP, PE or the like, a copolymer of PP and PE, SIS, SBS, hydrogenated SIS (SEPS), hydrogenated SBS (SEBS) and the like, which are the same as those employed for the first embodiment. From the viewpoint of thermal stability, SEPS and ESBS are especially preferable.

As a liquid conveyable material which renders both the first fabric base material and the second fabric base material permeable, a hydrophilic polymer is employed. The hydrophilic polymer can be obtained by melting a heat fusible polymer and mixing therewith a suitable active surface agent having a good compatibility. Such a heat fusible polymer, includes polyolefins such as PP, PE, a copolymer of PP and PE, SIS, SBS, hydrogenated SIS (SEPS), hydrogenated SBS (SEBS) and the like, which are the same as the above described heat fusible polymer. These may be employed alone or in various combinations. In particular, the above SEPS and SEBS can be preferably employed due to their thermal stability. For example, a water soluble polymer is not preferable as the liquid conveyable material because such a polymer dissolves upon contact with moisture -so as to cause blocking of the texture of the fabric base material.

As the surface active agent, which imparts a hydrophilic property, for mixing with the heat fusible polymer, there are preferably used nonionic surface active agents having one or two esters, such as a fatty acid ester of polyethylene glycol or glycerine nonionic surface active agents, such as a block copolymer of polyethylene glycol and polypropylene glycol. The above surface active agent provided in an amount of between 0.3 and 20% of the whole hydrophilic polymer (heat fusible polymer plus surface active agent), which is the liquid conveyable material, preferably between 0.5 and 10%. The same is kneaded with the heat fusible polymer, for example, at a high temperature. Thus, the hydrophilic polymer as the liquid conveyable material can be obtained.

A method of forming a liquid absorbing sheet material of the second embodiment will now be described. A hydrophilic polymer (liquid conveyable material) is prepared by melting a surface active agent and mixing it into a heat fusible polymer. Then, as shown in FIG. 4, a non-woven fabric sheet is transported in a direction of arrow B from a roll 10 containing a wound non-woven fabric sheet. A first thermoplastic polymer 12 is sprayed, with a spraying apparatus 13, on the reverse side of the non-woven fabric 11, which forms a new second non-woven fabric layer, resulting in a non-woven fabric 14 of a two-layer structure. In this way, a non-woven fabric 14 of a two-layer structure for sheet material can be prepared. The method of forming this two-layer structure sheet material is now described in detail. A heat fusible polymer 12 is sprayed over the reverse side of a non-woven fabric sheet 11 travelling in direction of arrow B. As shown in FIG. 5, air is blown about a melted heat fusible polymer 12 from exit 28 in a direction of the arrows. After exiting exit 28 of applicator 13, the heat fusible polymer 12 is thus converted into a fibrous state and sprayed over the non-woven fabric 11, so as to form the second non-woven fabric layer.

Then, the liquid absorbing sheet material can be manufactured by melting the hydrophilic polymer 16 (FIG. 6) with heat and spraying it over the reverse side of the two-layer structure non-woven fabric 14 (two-layer structure of non-woven fabric sheet 11 plus the second non-woven fabric layer). Hydrophilic polymer 16 is sprayed over the reverse side of non-woven fabric 14, and penetrates by providing a vacuum 17 beneath the non-woven fabric 14 of two-layer structure, travelling in a direction of an arrow B. At that time, air is blown about the melted hydrophilic polymer 16, as shown in FIG. 6, from exit 19 in a direction of an arrow soon after the melted hydrophilic polymer is blown out of an exit 19 of applicator 18. The hydrophilic polymer 16 is thus converted into a form of fibrous bodies, which are blown over the reverse side of non-woven fabric 14 of two-layer structure and penetrate the non-woven fabric 14.

As a method of spraying of the heat fusible polymer 12 and hydrophilic polymer 16, an applicator having a polymer blower may be used. As such an applicator having a polymer blower, there are hot melt sprayers, spiral sprayers and the like. As shown in FIG. 3, when employing a melt blown applicator for non-woven fabric manufacturing, uniform spraying on the polymer can be realized regardless of the line speed.

A liquid absorbing sheet material, thus obtained, as shown in FIG. 7, has a fibrous body with a hydrophilic polymer 16 penetrating and scattered into the fibers 20 of a two-layer non-woven fabric 14, which to pass through from the reverse to the surface side. The thickness of the hydrophilic polymer 16 should be within about 0.3 to 3 denier. Preferably, the thickness of the second non-woven fabric layer formed with a heat fusible polymer 12 is set within 0.15 to 3.0 mm.

A sanitary article of the present invention, as shown in FIG. 8, can be obtained by arranging a mat type water absorbing material 22 on the reverse side of a liquid absorbing sheet material 21 obtained in the above method. The thickness of the mat type water absorbing material 22, is usually between about 5 to 10 mm. The total thickness of the liquid absorbing sheet material 21 and mat type water absorbing material 22 is usually between about 5 to 13 mm.

By use of an adhesive property of the liquid conveyable material of a fibrous body scattered in the liquid absorbing sheet material 21, it is possible not only to improve the permeability of liquid, but also adhering of the liquid absorbing sheet material 21 and mat type water absorbing material 22 arranged on the reverse side.

As a mat type water absorbing material 22, there are no limitation, and conventional known materials may be employed. For example, one may use a sheet obtained by forming a high water absorbing polymer comprising pulp and sodium polyacrylate into the form of a sheet.

EFFECT OF THE INVENTION

As mentioned hereinbefore, the present invention is related to liquid absorbing sheet material wherein a fibrous body comprising a liquid conveyable material extending from the reverse side to the surface in the fabric tissue of the fabric base material. Also, the present invention is related to liquid absorbing sheet material of a two-layer structure comprising a first fabric base material and a second fabric base material made of a heat fusible polymer, laminated on the fabric base material, wherein a fibrous body of liquid conveyable material is scattered. The liquid absorbing sheet material retains an excellent permeability even though liquid may several times contact and pass thereinto, resulting in a dry surface of the sheet material being maintained. Liquid on the surface of liquid absorbing sheet material can be led to the fibrous body without staying on the surface and pass to and be absorbed by the absorbing sheet material arranged of the reverse side. In addition, since the fibrous body penetrating the above liquid absorbing sheet material has an adhesive effect, the sheet material and mat type water absorbing material arranged on the reverse side can be adhered when manufacturing a sanitary article by arranging the mat type absorbing material on the liquid absorbing sheet material. When adhering these two materials, another troublesome process such as installing an adhesive layer between them can be abbreviated, resulting in decreased cost and simplification of a manufacturing process and the structure of the product. Among such liquid absorbing sheet materials, two-layer liquid absorbing sheet material comprising a first fabric base material and a second fabric base material made of a heat fusible polymer, laminated on one side of the fabric base material can be manufactured by forming the second new fabric base material with a sprayed heat fusible polymer on the reverse side of the first fabric base material. The fibrous body comprising a liquid conveyable material is then sprayed thereon so that the liquid conveyable material penetrates both tissues of the first fabric base material and the second fabric base material. Therefore, the thickness of thus obtained liquid absorbing sheet material or two-layer structure sheet material is thick and uniform. Concomitantly, a thin fabric base material can be employed as base. By increasing the turning number on a roll and making the length of sheet of a roll longer, productivity can be improved due to a decrease of the number of times necessary to lower the transportation speed in roll shifting. The sanitary articles employing such liquid absorbing sheet material are most suitable for materials of, for example, a disposable diaper, a sanitary napkin, surgical absorbing sheet or the like.

The following examples and comparative examples are further illustrative of the invention.

(1) Liquid absorbing sheet material of the first embodiment was manufactured.

EXAMPLES 1 TO 9

Figure 1:
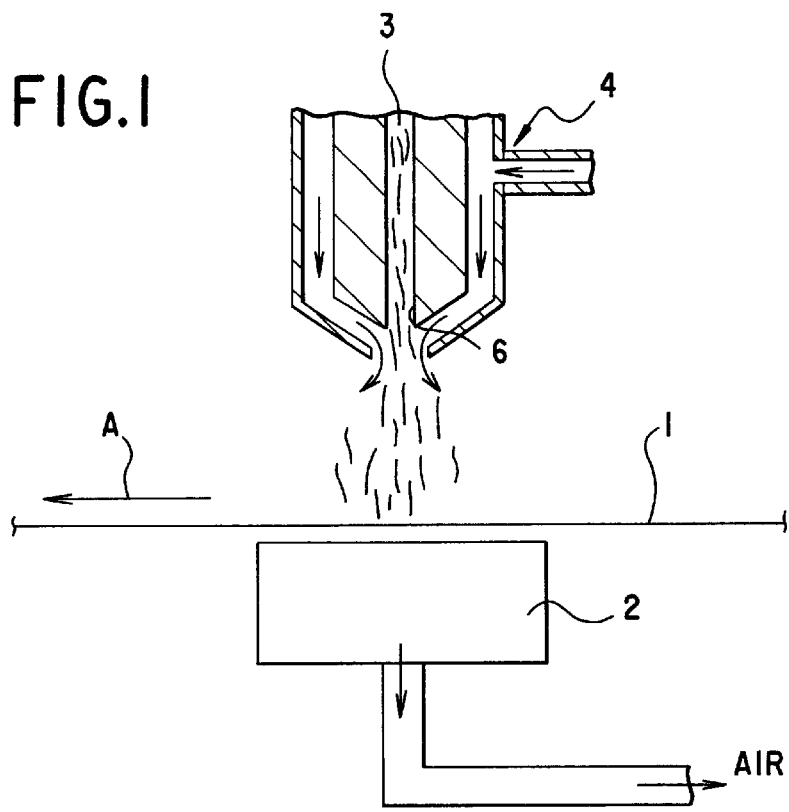
FIG. 1 illustrates one embodiment of a manufacturing process of a liquid absorbing sheet material of the present invention.
Figure 2:
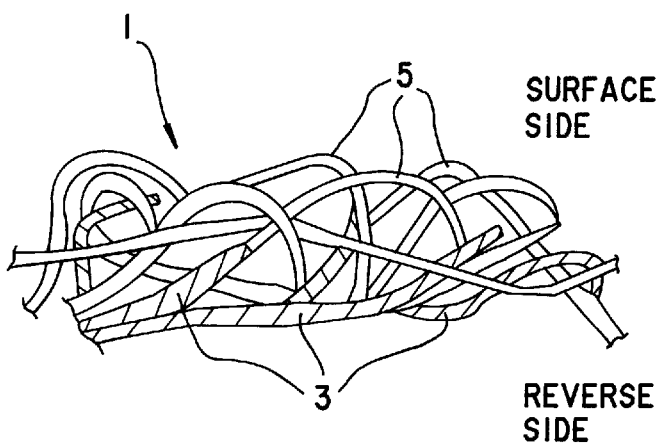
FIG. 2 is a diagrammatic illustration of a structure of a liquid absorbing sheet material of the present invention.

A polymer was prepared by melting and kneading each component shown in the following Table 1. Also, a nonwoven fabric of METSUKE volume at 20 g/m² was prepared. As shown in FIG. 1, the above polymer 3 was sprayed over the reverse side of a non-woven fabric 1, travelling in a direction of arrow A, while being absorbed in a direction of an arrow shown by use of a vacuum apparatus 2 installed under the non-woven fabric 1. The following liquid absorbing sheet materials were prepared.

TABLE 1

| | | EXAMPLE | | | | | | | |
|---|---|---|---|---|---|---|---|---|---|
| | 1 | 2 | 3 | 4 | 5 | 6 | 7 | 8 | 9 |
| POLYOLEFIN RESIN *1 | | | | | | | | | |
| A | 80 | — | — | 50 | — | — | — | — | — |
| B | — | 90 | — | — | 40 | 25 | — | — | — |
| C | — | — | 99 | 30 | 40 | 70 | — | — | — |
| D | — | — | — | — | — | — | 95 | — | 97 |
| E | — | — | — | — | — | — | — | 85 | — |

TABLE 1-continued

| | | EXAMPLE | | | | | | | |
|---|---|---|---|---|---|---|---|---|---|
| | 1 | 2 | 3 | 4 | 5 | 6 | 7 | 8 | 9 |
| SURFACE ACTIVE AGENT | | | | | | | | | |
| A *2 | 20 | 10 | 1 | 15 | 20 | 5 | 5 | 15 | — |
| B *3 | — | — | — | — | — | — | — | — | 3 |
| ANTIOXIDANT *4 | | | | | | | | | |
| | 0.5 | 0.5 | 0.5 | 0.5 | 0.5 | 0.5 | 0.5 | 0.5 | 0.5 | 0.5 |

(NB)
*1 polypropylene-polyethylene copolymer
*2 polyethylene glycol-fatty acid ester
*3 glycerine fatty acid ester
*4 phenol

COMPARATIVE EXAMPLES 1 to 6

Instead of the above heat fusible polymer, a water soluble polymer shown in the following Table 2 was employed. In the same way, except for that, liquid absorbing sheet materials were manufactured.

TABLE 2

| | | COMPARATIVE EXAMPLES | | | | |
|---|---|---|---|---|---|---|
| | 1 | 2 | 3 | 4 | 5 | 6 |
| WATER SOLUBLE POLYMER | | | | | | |
| A *1 | 100 | — | — | — | — | — |
| B *2 | — | 100 | — | — | — | — |
| C *3 | — | — | 100 | — | — | — |
| D *4 | — | — | — | 100 | — | — |
| E *5 | — | — | — | — | 100 | — |
| F *6 | — | — | — | — | — | 100 |
| ANTIOXIDANT *7 | | | | | | |
| | 0.5 | 0.5 | 0.5 | 0.5 | 0.5 | 0.5 |

(NB)
*1 polyethylene glycol
*2 polyethylene glycol
*3 polyethylene glycol
*4 polyvinyl pyrrolidone-vinyl acetate copolymer
*5 ethylene oxide-propylene oxide copolymer
*6 ethylene oxide-propylene oxide copolymer
*7 phenol

CONVENTIONAL EXAMPLE 1

A non-woven fabric of METSUKE 20 g/m² was prepared, and a nonionic surface active agent (Nonipole 500: Sanyokasei-sha product) was sprayed thereon.

Artificial urine was dropped on thus obtained examples and comparative examples so as to measure each contact angle. The results were shown in the following Tables 3 to 6. In addition, when measuring the contact angle, each liquid absorbing sheet material, which had been left untreated, in water of 20° C., in water of 40° C. and in water of 60° C. for a week respectively.

Evaluation of the liquid absorbing property was measured as follows. First, 50 cc of blue-colour artificial urine was dropped on each non-woven fabric so as to measure the time taken to absorb the urine (initial value). Subsequently, five minutes later, another 50 cc of blue-colour artificial urine was dropped in the same as the above so as to measure the time taken to absorb the urine by visual examination. Further, another five minutes later 50 cc of blue-colour artificial urine was dropped to measure the absorbing time. Thus, the change of the time was measured on each non-woven fabric by this repetition. The results were shown in the following Tables 3 to 6. After the above measurement, panelists valued the feel of the material by touching each surface of the non-woven fabric. o means dry feeling while X means wet feeling in Tables 3 to 6.

TABLE 3

|  | EXAMPLES | | | | |
|---|---|---|---|---|---|
|  | 1 | 2 | 3 | 4 | 5 |
| CONTACT ANGLE (°) | | | | | |
| untreated | 0 | 0 | 0 | 0 | 0 |
| left in water (20° C.) for 1 week | 0 | 0 | 0 | 0 | 0 |
| left in water (40° C.) for 1 week | 0 | 0 | 5 | 0 | 0 |
| left in water (60° C.) for 1 week | 0 | 0 | 7 | 0 | 0 |
| LIQUID ABSORBING PROPERTY (seconds) | | | | | |
| at the initial stage | <1 | <1 | <1 | <1 | <1 |
| 50 cc of artificial urine was dropped | <1 | <1 | <1 | <1 | <1 |
| 100 cc of artificial urine was dropped | <1 | <1 | <1 | <1 | <1 |
| FEEL OF SURFACE | 0 | 0 | 0 | 0 | 0 |

TABLE 4

|  | EXAMPLES | | | |
|---|---|---|---|---|
|  | 6 | 7 | 8 | 9 |
| CONTACT ANGLE (°) | | | | |
| untreated | 0 | 0 | 0 | 0 |
| left in water (20° C.) for 1 week | 0 | 0 | 0 | 0 |
| left in water (40° C.) for 1 week | 3 | 3 | 5 | 5 |
| left in water (60° C.) for 1 week | 3 | 3 | 7 | 5 |
| LIQUID ABSORBING PROPERTY (seconds) | | | | |
| at the initial stage | <1 | <1 | <1 | <1 |
| 50 cc of artificial urine was dropped | <1 | <1 | <1 | <1 |
| 100 cc of artificial urine was dropped | <1 | <1 | <1 | <1 |
| FEEL OF SURFACE | 0 | 0 | 0 | 0 |

TABLE 5

|  | COMPARATIVE EXAMPLES | | | | |
|---|---|---|---|---|---|
|  | 1 | 2 | 3 | 4 | 5 |
| CONTACT ANGLE (°) | | | | | |
| untreated | 15 | 20 | 10 | 30 | 40 |
| left in water (20° C.) for 1 week |  | dissolved | | | |
| left in water (40° C.) for 1 week | — | — | — | — | — |
| left in water (60° C.) for 1 week | — | — | — | — | — |
| LIQUID ABSORBING PROPERTY (seconds) | | | | | |
| at the initial stage | <1 | <1 | <1 | <1 | <1 |
| 50 cc of artificial urine was dropped | >30 | >30 | >30 | >30 | >30 |
| 100 cc of artificial urine was dropped | >30 | >30 | >30 | >30 | >30 |
| FEEL OF SURFACE | X | X | X | X | X |

TABLE 6

|  | COMPARATIVE EXAMPLE 6 | CONVENTIONAL EXAMPLE 1 |
|---|---|---|
| CONTACT ANGLE (°) | | |
| Untreated | 40 | 30 |
| left in water (20° C.) for 1 week | dissolved | 85 |
| left in water (40° C.) for 1 week | — | 90 |
| left in water (60° C.) for 1 week | — | 90 |
| LIQUID ABSORBING PROPERTY (seconds) | | |
| at the initial stage | <1 | <1 |
| 50 cc of artificial urine was dropped | >30 | >30 |
| 100 cc of artificial urine was dropped | >30 | >30 |
| FEEL OF SURFACE | X | 0 |

As clear from the above Tables 3 to 6, the water soluble polymer dissolved in COMPARATIVE EXAMPLES 1 to 6, so as to stuff the texture. In addition, although samples absorbed artificial urine in less than 1 second at the initial stage of the test for the liquid absorbing property, it took over 30 seconds, due to deterioration of liquid absorbing property, upon repeated dropping of artificial urine. Even untreated samples of COMPARATIVE EXAMPLES were large in contact angles and had poor liquid absorbing property. Compared with the COMPARATIVE EXAMPLES, EXAMPLES 1 to 9 were very small in contact angles and no deterioration of the absorbing time was shown not only at the initial stage, but also after twice dropping of artificial urine in which the time of absorbing was less than 1 second. In addition, the feel of surface in all EXAMPLES 1 to 9 was dry.

(2) Secondly, a sheet material as a base for the liquid absorbing sheet material in the second embodiment was prepared.

Five compounds for use as a heat fusible polymer were prepared as shown in the following Table 7.

TABLE 7

COMPOUNDS

HEAT FUSIBLE POLYMER a hydrogenated styrene-butadiene block copolymer (SEBS)
b hydrogenated styrene-isoprene block copolymer (SEPS)
c copolymer of polypropylene (PP) and polyethylene (PE)
d polyethylene (PE)
e polypropylene (PP)

EXAMPLE 10

Figure 3:
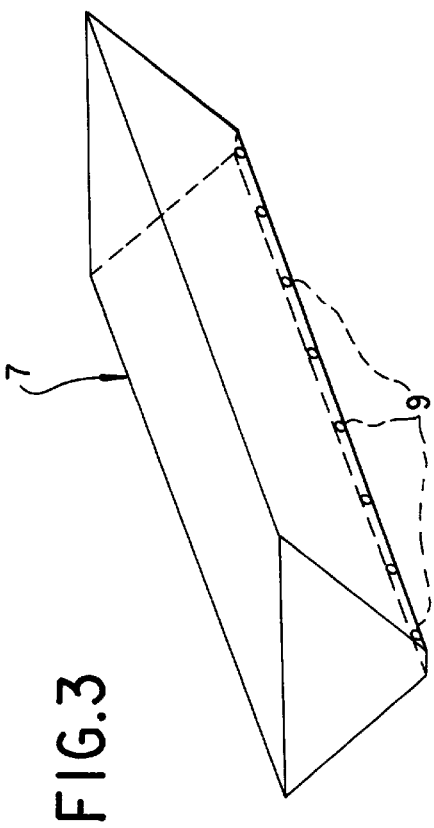
FIG. 3 is a perspective view of a melt-blown applicator.
Figure 9:
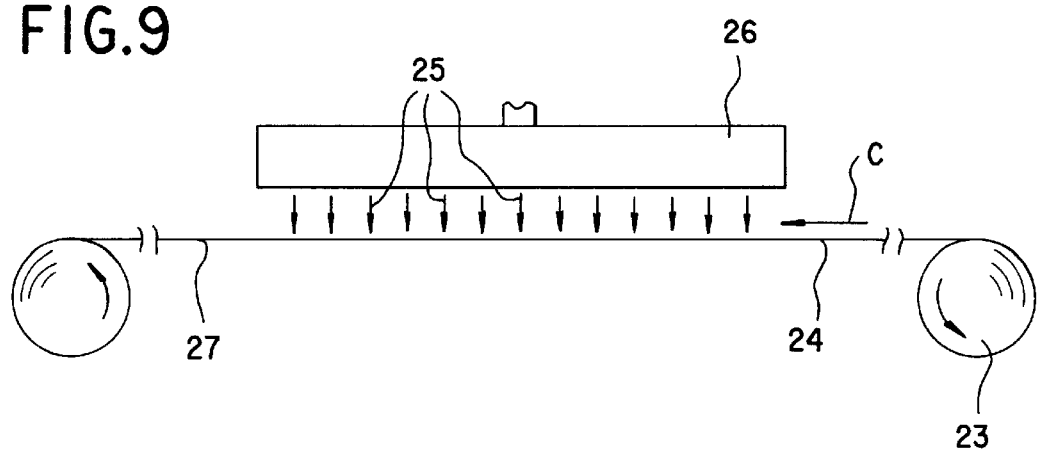
FIG. 9 illustrates a manufacturing process of a sheet material of the present invention.
Figure 10:
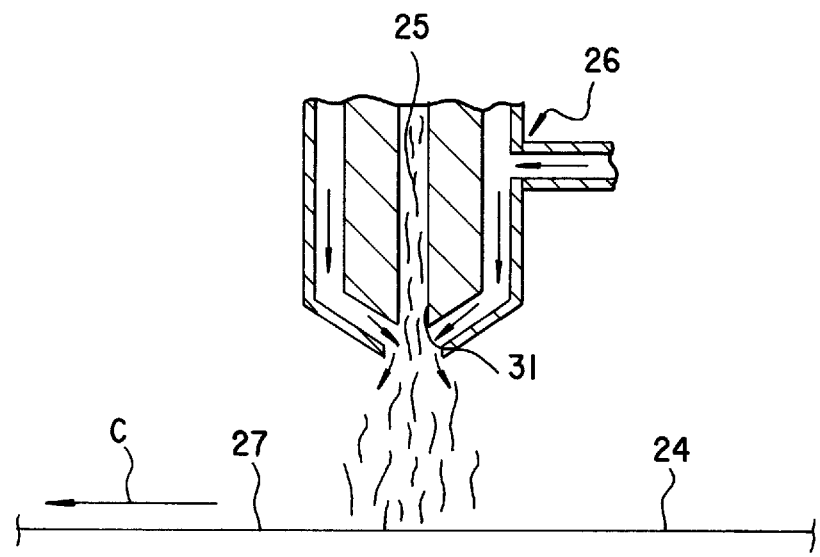
FIG. 10 illustrates how a polymer exit emits a heat fusible polymer.
Figure 11:
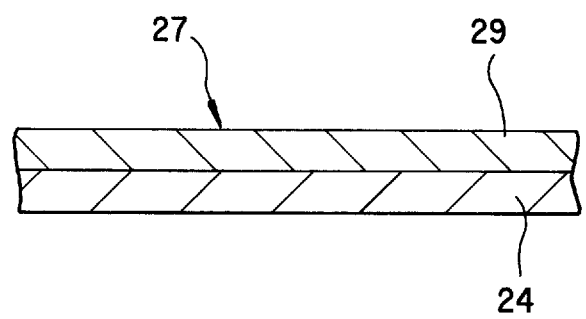
FIG. 11 is a sectional view of the above sheet material.

A roll was prepared having a non-woven fabric sheet of 15 g/m² for METSUKE volume. As shown in FIG. 9, the non-woven fabric 24 was drawn out from the roll 23 so as to be transported in a direction of arrow C. During transportation, the above heat fusible polymer 25 (heat fusible polymer a) which was melted and converted into fibrous body, was sprayed on the reverse side of the non-woven fabric 24 so as to form the second non-woven fabric layer. As shown in FIG. 10, air was blown about the heat fusible polymer 25 in a direction of an arrow from exit 31. After being emitted from an exit 31, the heat fusible polymer 25 was converted into a fibrous body, which was sprayed on non-woven fabric 24, forming the second non-woven fabric layer. A melt blown applicator such as shown in FIG. 3 was employed for spraying of the heat fusible polymer 25. As shown in FIG. 11, a two-layer structure sheet material 27 was formed, wherein the second non-woven fabric layer 29 comprising a heat fusible polymer 25 was laminated.

EXAMPLE 11

A heat fusible polymer b of the Table 7 was employed as a heat fusible polymer. Except for that, a sheet material was prepared in the same way as EXAMPLE 10.

EXAMPLE 12

A heat fusible polymer c of the Table 7 was employed as a heat fusible polymer. Except for that, a sheet material was prepared in the same way as EXAMPLE 10.

EXAMPLE 13

A mixture of heat fusible polymers a and c (mixing ratio (by weight); a:c=5.3) of the Table 7 was employed as a heat fusible polymer. Except for that, a sheet material was prepared in the same way as EXAMPLE 10.

EXAMPLE 14

A mixture of heat fusible polymers b and c (mixing ratio (by weight); b:c=1:1) of the Table 7 was employed as a heat fusible polymer. Except for that, a sheet material was prepared in the same way as EXAMPLE 10.

EXAMPLE 15

A mixture of heat fusible polymers b and c (mixing ratio (by weight); b:c=25:70) of the Table 7 was employed as a heat fusible polymer. Except for that, a sheet material was prepared in the same way as EXAMPLE 10.

EXAMPLE 16

A heat fusible polymer d of the Table 7 was employed as a heat fusible polymer. Except for that, a sheet material was prepared in the same way as EXAMPLE 10.

EXAMPLE 17

A heat fusible polymer e of the Table 7 was employed as a heat fusible polymer. Except for that, a sheet material was prepared in the same way as EXAMPLE 10.

The sheet material of EXAMPLES 10 to 17 and an untreated non-woven fabric on the market (METSUKE volume 12 g/m$^2$) (conventional example 2) were compared in different thicknesses. In addition, a commercially available thick non-woven fabric wound on a roll (METSUKE volume 25 g/m$^2$) (conventional example 3) was compared in thickness. The results are shown in the following Tables 8 and 9.

TABLE 8

| EXAMPLES | | | | | | | |
|---|---|---|---|---|---|---|---|
| 10 | 11 | 12 | 13 | 14 | 15 | 16 | 17 |
| THICKNESS OF SHEET MATERIAL (mm) | | | | | | | |
| 0.15 | 0.20 | 0.22 | 0.17 | 0.17 | 0.20 | 0.20 | 0.18 |

TABLE 9

| | CONVENTIONAL EXAMPLES | |
|---|---|---|
| | 2 | 3 |
| THICKNESS OF SHEET MATERIAL (mm) | 0.10 | 0.17 |

As clear from the results of Tables 8 and 9, in spite of the fact that the thickness of a non-woven fabric is of a METSUKE volume 15 g/m$^2$ at the initial material, the thickness became thick and surface was uniform. That is, a thickness more than that of a non-woven fabric in conventional example 3 was obtained.

(3) Then, liquid absorbing sheet material of the second embodiment was manufactured.

EXAMPLES 18 to 25

Figure 4:
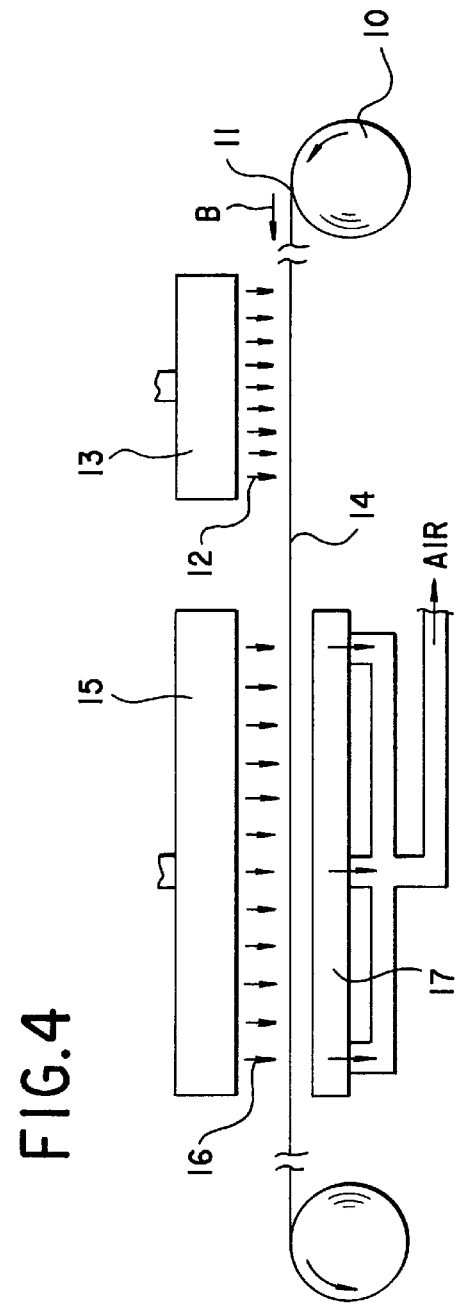
FIG. 4 illustrates another embodiment of a manufacturing process of a liquid absorbing sheet material of the present invention.
Figure 5:
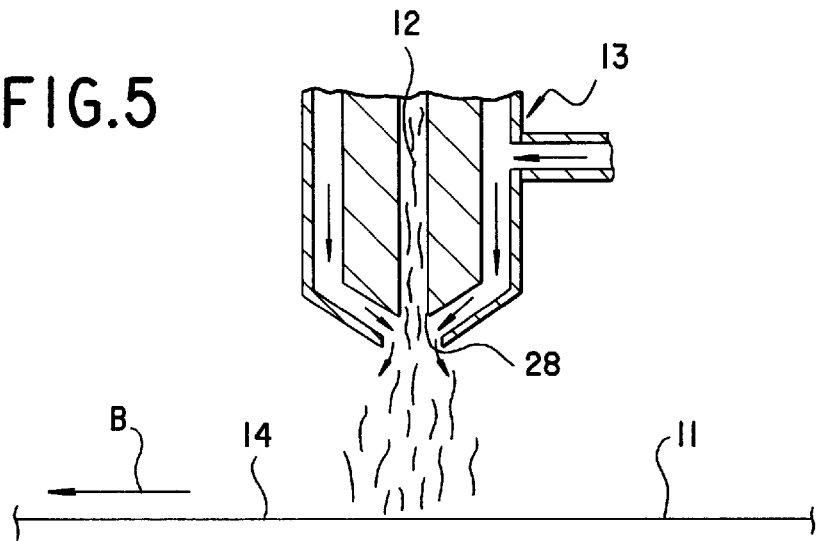
FIG. 5 illustrates how an applicator emits a heat fusible polymer in a manufacturing process of two-layer structure sheet material.
Figure 6:
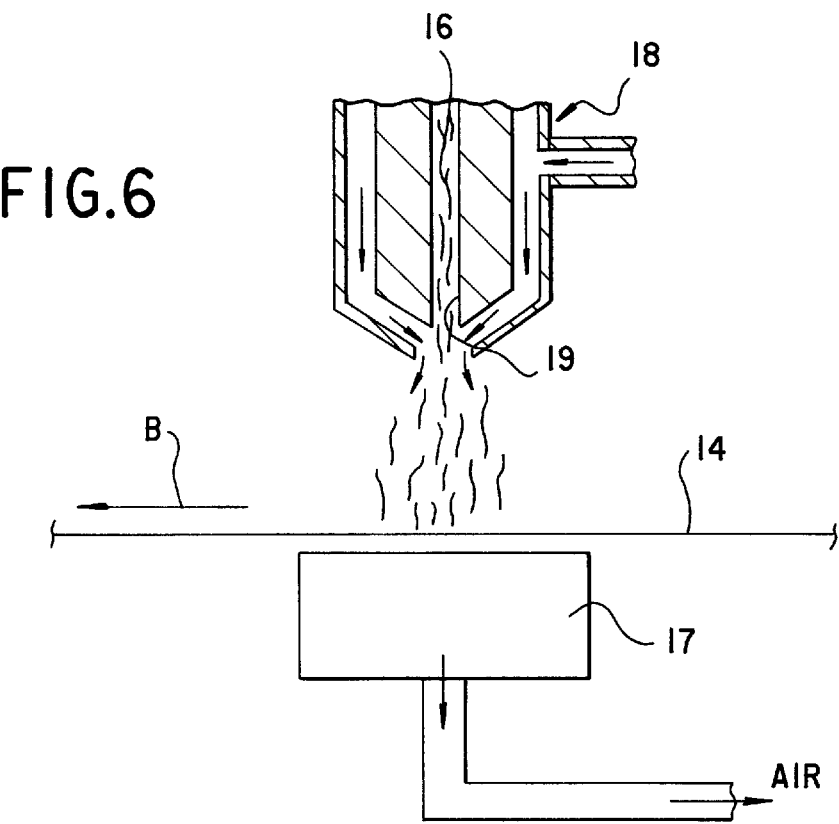
FIG. 6 illustrates how an applicator emits a heat fusible polymer.

A hydrophilic polymer was produced by melting each component shown in the following Table 10 for kneading. Also, a roll wherein having a wound non-woven fabric sheet of a METSUKE volume 15 g/m$^2$ was prepared. As shown in FIG. 4, a non-woven fabric sheet 11 was drawn out of the roll 10 in a direction of arrow B.

Figure 7:
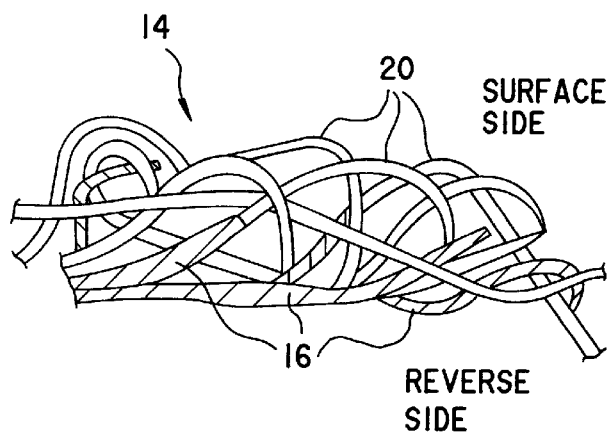
FIG. 7 is a diagrammatic illustration of another embodiment of a liquid absorbing sheet material.
Figure 8:
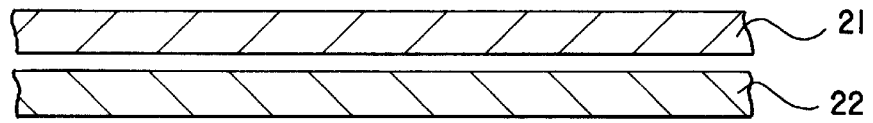
FIG. 8 shows a sectional view of a sanitary article of the present invention.

During movement, a heat fusible polymer of a polypropylene-polyethylene copolymer 12 was sprayed on the reverse side of the non-woven fabric sheet 11 from an applicator 13 having a polymer blower so as to form the second non-woven fabric layer 14. Then, heat was applied to the hydrophilic polymer 16 to melt the polymer and at the same time the polymer was sprayed over the reverse side of the two-layer structure of non-woven fabric 14 (two-layer structure of non-woven fabric sheet layer 11 and the second non-woven fabric layer) from a polymer emitter 15. At the same time, absorption was conducted by a vacuum device 17 established under two-layer non-woven fabric 14. The liquid absorbing sheet material was thus produced. The liquid absorbing sheet materials obtained were thick and had a uniform surface. From observation by an electron microscope, shown in FIG. 7, it is found that the hydrophilic polymer 16, which is converted into a fibrous body, penetrated among fiber 20 of the two-layer non-woven fabric 14 from one side to the other side.

TABLE 10

| | EXAMPLES | | | | | | | |
|---|---|---|---|---|---|---|---|---|
| | 18 | 19 | 20 | 21 | 22 | 23 | 24 | 25 |
| POLYOLEFIN RESIN *1 | | | | | | | | |
| A | 80 | — | — | 50 | — | — | — | — |
| B | — | 90 | — | — | 40 | 25 | — | — |
| C | — | — | 99 | 30 | 40 | 70 | — | — |
| D | — | — | — | — | — | — | 95 | — |
| E | — | — | — | — | — | — | — | 85 |
| SURFACE ACTIVE AGENT *2 | 20 | 10 | 1 | 20 | 20 | 5 | 5 | 15 |
| ANTIOXIDANT *3 | 0.5 | 0.5 | 0.5 | 0.5 | 0.5 | 0.5 | 0.5 | 0.5 |

(NB)
*1 polypropylene-polyethylene copolymer
*2 polyethylene glycol-fatty acid ester
*3 phenol

CONVENTIONAL EXAMPLE 4

A non-woven fabric of METSUKE volume 15 g/m$^2$ was prepared. A nonionic surface active agent (Nonipole 500, Sanyokasei-sha product) was sprayed on the reverse side of the fabric to produce a liquid absorbing sheet material having a nonionic surface active agent.

The examples obtained and conventional example 4 were measured as to their contact angles by dropping on artificial urine. The results are shown in the following Tables 11 and 12. When measuring the contact angles, other liquid absorbing sheet materials, were left untreated, in water of 20° C., 40° C. and 60° C. for a week.

Evaluation tests of the liquid absorbing property were conducted. The time taken to absorb 50 cc of blue-colour artificial urine dropped on each non-woven fabric was measured (initial evaluation). Five minutes later, another 50 cc of blue-colour artificial urine was dropped, as above, so as to measure the time taken to absorb the urine by visual examination. Further, five minutes later an additional 50 cc of blue-colour artificial urine was dropped to measure the time for absorbing. The change of the time of absorption was measured on each non-woven fabric by this repetition. The results are shown in the following Tables 11 and 12. After the above measurement, panelists evaluated each non-woven fabric by feel, by touching each surface. ○ means a dry feel while X means a wet feel in Tables 3 to 6.

TABLE 11

|  | EXAMPLES | | | | |
| --- | --- | --- | --- | --- | --- |
|  | 18 | 19 | 20 | 21 | 22 |
| CONTACT ANGLE (°) | | | | | |
| untreated | 0 | 0 | 0 | 0 | 0 |
| left in water (20° C.) for 1 week | 0 | 0 | 0 | 0 | 0 |
| left in water (40° C.) for 1 week | 0 | 0 | 5 | 0 | 0 |
| left in water (60° C.) for 1 week | 0 | 0 | 7 | 0 | 0 |
| LIQUID ABSORBING PROPERTY (seconds) | | | | | |
| at the initial stage | <1 | <1 | <1 | <1 | <1 |
| 50 cc of artificial urine was dropped | <1 | <1 | <1 | <1 | <1 |
| 100 cc of artificial urine was dropped | <1 | <1 | <1 | <1 | <1 |
| FEEL OF SURFACE | ○ | ○ | ○ | ○ | ○ |
| THICKNESS OF WHOLE SHEET MATERIAL (mm) | 0.17 | 0.22 | 0.25 | 0.20 | 0.22 |

TABLE 12

|  | EXAMPLES | | | CONVENTIONAL EXAMPLE |
| --- | --- | --- | --- | --- |
|  | 23 | 24 | 25 | 4 |
| CONTACT ANGLE (°) | | | | |
| untreated | 0 | 0 | 0 | 30 |
| left in water (20° C.) for 1 week | 0 | 0 | 0 | 85 |
| left in water (40° C.) for 1 week | 3 | 3 | 5 | 90 |
| left in water (60° C.) for 1 week | 3 | 3 | 7 | 90 |
| LIQUID ABSORBING PROPERTY (seconds) | | | | |
| at the initial stage | <1 | <1 | <1 | <1 |
| 50 cc of artificial urine was dropped | <1 | <1 | <1 | >30 |
| 100 cc of artificial urine was dropped | <1 | <1 | <1 | >30 |
| FEEL OF SURFACE | ○ | ○ | ○ | X |
| THICKNESS OF WHOLE SHEET MATERIAL (mm) | 0.23 | 0.23 | 0.20 | 0.10 |

As clear from the above Tables 11 and 12, although samples absorbed artificial urine in less than 1 second at the initial stage, it took at least 30 seconds due to deterioration of liquid the absorbing property with repeated dropping of artificial urine. Even untreated samples of CONVENTIONAL EXAMPLE were large in contact angles and had a poor liquid absorbing property. Compared with CONVENTIONAL EXAMPLE 4, each of the EXAMPLES were very small in contact angles and no deterioration of absorbing time was shown not only at the initial stage, but also after twice dropping of artificial urine in which the time of absorbing was less than 1 second. In addition, the surface feel of all the EXAMPLES was dry. Further, in spite that a non-woven fabric at a low METSUKE volume of 15 g/m$^2$ was employed, a final thickness was achieved as in the case which employed a thick METSUKE volume.

What is claimed is:

1. A liquid absorbing sheet material comprising a fabric base material having a first side and a second side, and having dispersed therein fibers of a liquid conveyable material of a heat fusible polymer, said fibers extending through the thickness of the fabric base material from the second side to the first side of the fabric base material, and further containing a surface active agent accounting for 0.1 to 20% by weight of the total liquid conveyable material.

2. A liquid absorbing sheet material according to claim 1, wherein the fabric base material weighs 15 to 60 g/m$^2$.

3. A liquid absorbing sheet material according to claim 1, wherein the heat fusible polymer is at least one of polypropylene, polyethylene, a copolymer of propylene and ethylene, a styrene-isoprene block copolymer, a styrene-butadiene block copolymer, a hydrogenated styrene-isoprene block copolymer or a hydrogenated styrene-butadiene block copolymer.

4. A sanitary article wherein a water absorbing mat material is arranged on the second side of the liquid absorbing material according to any of claims 1, 2, or 3.

5. A two-layer liquid absorbing sheet material comprising a first fabric base material having a first side and a second side, and a second fabric base material of a heat fusible polymer having a first side and a second side, wherein the first side of the second fabric base material is laminated to the second side of the first fabric base material, said two-layer sheet material having dispersed therein fibers of a liquid conveyable material, said fibers extending through the first and second fabric base materials from the second side of the second fabric material into the first fabric base material; and a water absorbing mat material arranged on the second side of the second fabric base material in the liquid absorbing sheet material.

6. A two-layer liquid absorbing sheet material according to claim 5, wherein the first fabric base material weighs 15 to 60 g/m$^2$.

7. A liquid absorbing sheet material according to claim 5, wherein the liquid conveyable material is a heat fusible polymer containing a surface active agent.

8. A liquid absorbing sheet material according to claim 7, wherein the heat fusible polymer is at least one of polypropylene, polyethylene, a copolymer of propylene and ethylene, a styrene-isoprene block copolymer, a styrene-lutadiene block copolymer, a hydrogenated styrene-isoprene block copolymer or a hydrogenated styrene-butadiene block copolymer.

* * * * *

UNITED STATES PATENT AND TRADEMARK OFFICE
CERTIFICATE OF CORRECTION

PATENT NO.:   5,807,370
DATED     :   Sep. 15, 1998
INVENTOR(S):  Igaue et al.

It is certified that error appears in the above-identified patent and that said Letters Patent is hereby corrected as shown below:

Column 14, line 46, in Claim 5;  add --base-- between "fabric" and "material".

Column 14, line 53, in Claim 7, insert --two-layer-- between "a" and "liquid".

Column 14, line 56, in Claim 8, insert --two-layer-- between "A" and "liquid".

Column 14, line 60, in Claim 8, change "lutadiene" to read --butadiene--.

Signed and Sealed this

Eighth Day of August, 2000

Q. TODD DICKINSON

*Attest:*

*Attesting Officer*         *Director of Patents and Trademarks*